United States Patent
Dubac et al.

(12) 
(10) Patent No.: US 6,184,418 B1
(45) Date of Patent: Feb. 6, 2001

(54) AROMATIC COMPOUND ACYLATION METHOD

(75) Inventors: Jacques Dubac, Pechbusque; Hafida Gaspard, Toulouse; Mireille Labrouillere, Agen; André Laporterie, Pompertuzat; Jean-Roger Desmurs, Saint-Symphorien-d'Ozon; Christophe Le Roux, Toulouse, all of (FR)

(73) Assignee: Rhodia Chimie, Courbevoie Cedex (FR)

( * ) Notice: Under 35 U.S.C. 154(b), the term of this patent shall be extended for 0 days.

(21) Appl. No.: 09/101,713

(22) PCT Filed: Sep. 24, 1996

(86) PCT No.: PCT/FR96/01488

§ 371 Date: Jan. 19, 1999

§ 102(e) Date: Jan. 19, 1999

(87) PCT Pub. No.: WO97/11930

PCT Pub. Date: Apr. 3, 1997

(30) Foreign Application Priority Data

Sep. 25, 1995 (FR) .................................. 95 11250

(51) Int. Cl.[7] .............................. C07C 45/46; C07F 9/94
(52) U.S. Cl. .................... 568/319; 568/323; 568/326; 568/328; 556/64
(58) Field of Search .................... 568/309, 319, 568/322, 326, 323, 328; 502/151, 152, 170, 171; 556/64

(56) References Cited

U.S. PATENT DOCUMENTS 3,883,594 * 5/1975 Schmerling ........................ 260/592
4,539,420 * 9/1985 Tsuchihashi et al. ................ 560/56

FOREIGN PATENT DOCUMENTS 067698  12/1982  (EP) .

OTHER PUBLICATIONS

*J. Chem. Soc., Chem., Commun.*, A. Kawada et al., "Lathanide trifluoromethanesulfonates as reusable catalysts: catalytic Friedel–Crafts acylation", vol. 14, pp. 1157–1158, 1993.

*Journal of the Chemical Society*, Y. Matano et al., "Synthesis, x–ray structure, thermal stability and reactions of triaryl(3–oxoalkyl)bismuthonium salts", No. 20, pp. 2543–2549, 1995.

*Indian J. Chem*, S. Singh et al., "Trifluoromethanesulfonates of antimony(III) and bismuth(III)", vol. 22a, pp. 814–815, 1983.

*J. Fluorine Chem.*, D. Niyogi, et al., "Some reactions of trifluoromethanesulfonic anhydride with various metal substrates", vol. 48, pp. 421–428, 1990.

*Journal of Fluorine Chemistry*, D. Debyani, et al., "Reaction of fluorinated acid anhydrides, (CF3CO)2O, (CF3S02)2O and (FS02)2O, with organometallic substrates of group 15 (As, Sb and Bi)", vol. 70, pp 237–240, 1995.

* cited by examiner

Primary Examiner—Sreeni Padmanabhan
(74) Attorney, Agent, or Firm—Burns, Doane, Swecker & Mathis, L.L.P.

(57) ABSTRACT

A method for acylating an aromatic compound, specifically an activated or deactivated aromatic compound, is disclosed. The method is suitable for preparing aromatic ketones. The preparation of a catalyst and novel bismuth compounds is also disclosed. Said aromatic compound acylation method comprises reacting said aromatic compound with an acylating agent in the presence of a catalyst, and is characterised in that the acylation reaction is performed in the presence of an effective amount of at least one bismuth salt of trifluoromethanesulphonic acid.

34 Claims, No Drawings

AROMATIC COMPOUND ACYLATION METHOD

This is the US National Stage Application of PCT/FR96/01488 filed Sep. 24, 1996.

This invention relates to a method for acylating an aromatic compound. More precisely, the invention refers to a method for acylating an activated or deactivated aromatic compound.

This invention is particularly interesting in the case of the acylation of a deactivated aromatic compound.

The invention is suitable for the preparation of aromatic ketones.

The invention also relates to the preparation of the catalyst and of new bismuth compounds.

In the following presentation of the invention, by "aromatic compound" we understand the conventional notion of aromaticity as defined in the literature, in particular by Jerry MARCH in Advanced Organic Chemistry, $4^{th}$ Edition, John Wiley and Sons, 1992, p 40 and following.

By "deactivated aromatic compound", we define an aromatic compound without substitutent, such as benzene for example, or an aromatic compound that contains one or several substitutents that deactivate the aromatic nucleus, such as electroattractive groups.

By "activated aromatic compound", we mean an aromatic compound consisting of one or more substitutents that activate the aromatic nucleus such as electron donor groups.

The notions of electron donor and electroattractive groups are defined in literature. One may refer, among others, to Jerry MARCH in Advanced Organic Chemistry, $4^{th}$ Edition, John Wiley and Sons, 1992, chapter 9, pp. 273–292.

A standard method for the preparation of aromatic ketones consists of performing an acylation reaction of the Freidel-Crafts sort.

A reaction of the aromatic compound and an acylation agent is performed in the presence of a catalyst, usually aluminum chloride.

An example of this type of method is shown in the works of C. Kuroda et al [Sci. Papers Inst. Phys. Chem. Res. 18, pp 51–60 (1932)] that have described the preparation of methoxyacetophenones, by reaction of an aromatic compound that carries from 1 to 3 methoxy groups, with acetyl chloride in the presence of aluminum chloride.

However, the use of aluminum chloride presents many inconveniences. Aluminum chloride is a corrosive and irritant product. Furthermore, it is necessary to use a large quantity of aluminum chloride, at least as much as the stoichiometry on account of the complexation of the ketone formed. Consequently, aluminum chloride is not a true catalyst.

At the end of the reaction, it is necessary to eliminate the aluminum chloride from the reaction solution by performing a basic or acid hydrolysis.

This hydrolysis involves adding water to the reaction solution, which appreciably complicates the implementation of the process since the metal cation, more specifically the aluminum cation, then forms aluminum polyoxo- and/or polyhydroxo-complexes of a milky consistency in the presence of water which are later difficult to separate. This results in the need to perform a long and costly treatment that consists, after the hydrolysis, of an extraction of the organic phase, a separation of the aqueous and organic phases, possibly even a drying of the latter. The separation of the aluminum chloride is therefore long and costly.

Besides, there is also the problem of saline aqueous runoffs that must later be neutralized, requiring an additional operation.

Furthermore, the aluminum chloride cannot be recycled because of the hydrolysis.

To avoid this inconvenience, Atsushi Kawada et al [J. Chem. Soc. Chem. Commun. Pp 1157–1158 (1993) and Synlett pp 545–546 (1994)] have proposed to perform the acylation reaction of an aromatic compound using an acetic anhydride in the presence of a catalytic quantity of trifluoromethanesulfonate of lanthanide, in particular ytterbium or scandium triflate.

The inconvenience of these catalysts is that they only allow the acylation of activated aromatic compounds, such as anisole.

These last references, as many catalysts described in prior art, do not address in a general way the acylation problems of aromatic substrates that are both activated as well as deactivated, and in conditions that are easy to implement.

This invention reaches this objective and gives a procedure to avoid the afore-mentioned inconveniences.

There is now, and this is what this invention pertains to, a method that will allow for the acylation of an aromatic compound that consists in making the said aromatic compound react with an acylation agent, in the presence of a catalyst characterized by the fact that the acylation reaction is performed in the presence of an effective quantity of at least one bismuth salt of triflic acid.

In this text, by "triflic acid" we mean the trifluoromethanesulfonic acid $CF_3SO_3H$.

As mentioned below, the invention calls for the use of tris-trifluoromethanesulfonate of bismuth as a catalyst as well as catalysts containing less than three trifluoromethanesulfonic anions for one bismuth cation.

Another element of the invention is the preparation process of the catalyst for the invention.

Lastly, another element of the invention relates to new bismuth compounds

More precisely, this invention relates to the acylation method of an aromatic compound that fits the general formula (I):

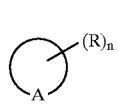

(I)

In which:
  A symbolizes the remainder of a cycle forming all or a part of a carbocyclic or heterocyclic system that is either aromatic, monocyclic, or polycyclic: said cyclic remainder may carry a radical R representing a hydrogen atom or one or several identical or different substitutents,
  n represents the number of substitutents on the cycle.

The invention applies in particular to aromatic compounds that match the formula (I) in which A is the remainder of a cyclic compound, having preferably at least 4 atoms in the cycle, possibly substituted, and representing at least one of the following cycles:
  A monocyclic or polycyclic aromatic carbocycle
  A monocyclic or polycyclic aromatic heterocycle containing at least one of the heteroatoms O, N and S.

More specifically, without however limiting the extent of the invention, the possibly substituted remainder A represents the remainder:
  1) of a monocyclic or polycyclic aromatic carbocyclic compound, by "polycyclic carbocyclic compound" we mean:

a compound consisting of at least 2 aromatic carbocycles that between them form ortho- or ortho- and peri-condensed systems, a compound consisting of at least 2 carbocycles of which only one is aromatic and that between them form ortho- or ortho- and peri-condensed systems 2) of a monocyclic or polycyclic aromatic heterocyclic compound, by "aromatic heterocyclic compound" we mean:

a compound consisting of at least 2 heterocycles containing at least one heteroatom in each cycle of which at least one of the two cycles is aromatic and that between them form ortho- or ortho- and peri-condensed systems a compound consisting of at least one hydrocarbonic cycle and at least one heterocycle of which at least one of the cycles is aromatic and that between them form ortho- or ortho- and peri-condensed systems.

3) of a compound composed of a chain of cycles, such as those defined in paragraphs 1 and/or 2 linked together:
by a valencial link,
by an alkylene or alkylidene radical with 1 to 4 carbon atoms, preferably a methylene or isopropylidene radical,
by one of the following groups

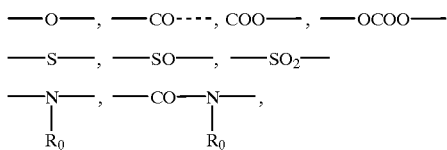

In these formulas, Ro represents a hydrogen atom or an alkyl radical with 1 to 4 carbon atoms, a cyclohexyl or phenyl radical.

As examples of cycles 1 to 3, let us cite:

1) Benzene, toluene, xylene, naphthalene, anthracene,
2) Furan, pyrrole, thiophene, isoxasole, furazan, isothiazole, imidazole, pyrazole, pyridine, pyridazine, pyrimidine, quinoline, naphtyridine, benzofuran, indole
3) Biphenyl, 1,1'-methylenebiphenyl, 1,1'-isopopylidenebiphenyl, 1,1'-oxybiphenyl, 1,1'-iminobiphenyl In the method of the invention, we preferably use a formula (I) aromatic compound in which A represents a benzene nucleus.

The formula (I) aromatic compound can carry one or several substitutents.

The number of substitutents present on the cycle depends on the carbon condensation of the cycle and on whether or not unsaturations are present on the cycle.

The maximum number of substitutents that can be carried by a cycle is easily determined by a professional in this field.

In this text, in general, by "several" we mean less than 4 substitutents on one aromatic nucleus. Examples of substitutents are given below, however, this list is by no means limiting. As mentioned previously, the substitutents may or may not activate the aromatic nucleus.

The remainder A may be a bearer of one or several substitutents that are represented in the formula (I) by the symbol R and whose preferred specifications are defined as follows:

the R radical(s) represent one of the following groups:
a hydrogen atom a linear or branched alkyl radical, with 1 to 6 carbon atoms, preferably 1 to 4 carbon atoms such as methyl, ethyl, propyl, isopropyl, butyl, isobutyl, sec-butyl, tert-butyl, a linear or branched alkenyl radical with 2 to 6 carbon atoms, preferably 2 to 4 carbon atoms, such as vinyl, allyl, a linear or branched alkoxy radical with 1 to 6 carbon atoms, preferably 1 to 4 carbon atoms such as methoxy, ethoxy, propoxy, isopropoxy, and butoxy radicals, a cyclohexyl radical, an acyl group with 2 to 6 carbon atoms, a radical with a formula:
—$R_1$—OH
—$R_1$—$COOR_2$
—$R_1$—CHO
—$R_1$—$NO_2$
—$R_1$—CN
—$R_1$—$N(R_2)_2$
—$R_1$—CO—$N(R_2)_2$
—$R_1$—X
—$R_1$—$CF_3$ In these formulas, $R_1$ represents a valencial link or a linear or branched, saturated or unsaturated divalent hydrocarbonic radical with 1 to 6 carbon atoms such as, for example, methylene, ethylene, propylene, isopropylene, isopropylidene; the identical or different $R_2$ radicals represent a hydrogen atom or a linear or branched alkyl radical with 1 to 6 carbon atoms; X symbolizes a halogen atom, preferably a chlorine, bromine, or fluorine atom.

When n is greater than or equal to 2, two radicals R and the 2 successive atoms of the aromatic cycle can be linked to each other by an alkylene, alkenylene or alkenylidene radical with 2 to 4 carbon atoms in order to form a saturated, unsaturated, or aromatic heterocycle with 5 to 7 carbon atoms. One or several carbon atoms can be replaced by another heteroatom, preferably oxygen. Thus, the radicals R can represent a methylene dioxy or an ethylene dioxy radical.

This invention is particularly applicable to aromatic compounds that fit the formula (I) in which:

The R radical(s) belong to one of the following groups:
a hydrogen atom,
an OH group,
a linear or branched alkyl radical with 1 to 6 carbon atoms,
a linear or branched alkenyl radical with 2 to 6 carbon atoms,
a linear or branched alkoxy radical with 2 to 6 carbon atoms,
a —CHO group,
an acyl group with 2 to 6 carbon atoms,
a —$COOR_2$ group where the specification of $R_2$ is defined above,
a —$NO_2$ group,
a —$NH_2$ group,
a halogen atom, preferably a fluorine, chlorine, or bromine atom,
a —$CF_3$ group, n is a number equal to either 0, 1, 2, or 3.

Among the compounds of formula (I), in particular those matching the following formulas are used:

a monocyclic or polycyclic aromatic carbocyclic compound with cycles that can form an orthocondensed system of formula (Ia) between them:

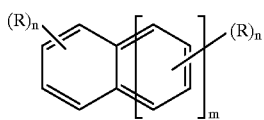

In this formula (Ia), m represents a number equal to 0, 1, or 2 and the symbols R, identical or different, and n have the meaning described previously.

a compound made by linking two or several monocyclic aromatic carbocycles matching formula (Ib):

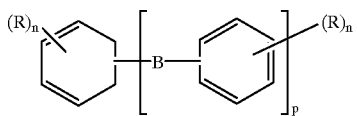

In said formula (Ib), symbols R, identical or different and n, have the meaning described previously; p is a number equal to 0, 1, 2, or 3 and B represents:
- a valencial link
- an alkylene or alkylidene radical with 1 to 4 carbon atoms, preferably a methylene or isopropylidene radical,
- one of the following groups

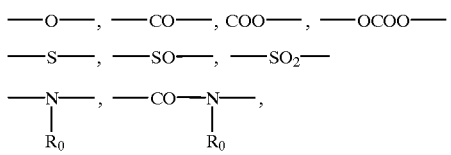

In these formulas, $R_0$ represents a hydrogen atom or an alkyl radical with 1 to 4 carbon atoms, a cyclohexyl or phenyl radical.

The preferred compounds of formula (I) match formulas (Ia) and (Ib) in which:
- R represents a hydrogen atom, a hydroxyl group, a —CHO group, a —$NO_2$ group, a —$NH_2$ group, a linear or branched alkyl or alkoxy radical with 1 to 6 carbon atoms, preferably 1 to 4 carbon atoms or one halogen atom,
- B symbolizes a valencial link, an alkylene or alkylidene radical with 1 to 4 carbon atoms or one oxygen atom.
- m is equal to 0 or 1,
- n is equal to 0, 1 or 2,
- p is equal to 0 or 1.

Even more preferably, we will choose the compounds of formula (I) in which R represents a hydrogen atom, a hydroxyl group, a methyl radical, a methoxy radical, or a halogen atom.

To illustrate the compounds that match formula (I), we have the following list:
- halogenated or non halogenated aromatic compounds such as benzene, toluene, chlorobenzene, dichlorobenzenes, trichlorobenzenes, fluorobenzene, diflurorobenzenes, chlorofluorobenzenes, chlorotoluenes, fluorotoluenes, bromobenzene, dibromobenzenes, bromofluorobenzenes, bromochlorobenzenes, trifluoromethylbenzene, trifluoromethoxybenzene, trichloromethylbenzene, trichloromethoxybenzene, trifluoromethylthiobenzene,
- aminated or nitrated aromatic compounds such as aniline and nitrobenzene,
- phenolic compounds such as phenol, o-cresol, guaiacol
- monoethers such as anisole, ethoxybenzene (phenetol), butoxybenzene, isobutoxybenzene, 2-chloroanisole, 3-chloroanisole, 2-bromoanisole, 3-bromoanisole, 2-methylanisole, 3-methylanisole, 2-ethylanisole, 3-ethylanisole, 2-isopropylanisole, 3-isopropylanisole, 2-propylanisole, 3-propylanisole, 2-allylanisole, 2-butylanisole, 3-butylanisole, 2-tert-butylanisole, 3-tert-butylanisole, 2-bezylanisole, 2-cyclohexylanisole, 1-bromo-2-ethoxybenzene, 1-bromo-3-ethoxybenzene, 1-chloro-2-ethoxybenzene, 1-chloro-3-ethoxybenzene, 1-ethoxy-2-ethylbenzene, 1-ethoxy-3-ethylbenzene, 2,3-dimethylanisole, 2,5-dimethylanisole,
- diethers such as veratrole, 1,3-dimethoxybenzene, 1,2-diethoxybenzene, 1,3-diethoxybenzene, 1,2-dipropoxybenzene, 1,3-dipropoxybenzene, 1,2-methylenedioxybenzene, 1,2-ethylenedioxybenzene,
- triethers such as 1,2,3-trimethoxybenzene, 1,3,5-trimethoxybenzene, 1,3,5-triethoxybenzene, The compounds which apply in a more interesting manner to the method of this invention are the benzene, toluene, phenol, anisole, and veratrole.

As far as the acylation reagent is concerned, it especially matches formula (II):

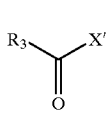

In which:
$R_3$ represents:
- a saturated or unsaturated, linear or branched aliphatic radical, with 1 to 24 carbon atoms; a saturated, unsaturated, or aromatic monocyclic or polycyclic cycloaliphatic radical with 4 to 12 carbon atoms; a saturated or unsaturated, linear or branched aliphatic radical bearing a cyclic substitutent, X' represents:
- a halogen atom, preferably a chlorine or bromine atom,
- a —O—CO—$R_4$ radical where $R_4$ is identical or different from $R_3$, with the same specification as $R_3$, By cyclic substitutent, we mean preferably a saturated, unsaturated, or aromatic carbocyclic cycle, preferably cycloaliphatic or aromatic, in particular cycloaliphatic containing 6 carbon atoms in the cycle or in the benzene.

More preferably, $R_3$ represents a linear or branched alkyl radical with 1 to 12 carbon atoms, preferably 1 to 6 carbon atoms: the hydrocarbon chain may possibly be interrupted by a heteroatom (for example, oxygen), by a functional group (for example —O—) and/or a group bearing a substitutent (for example a halogen or a $CF_3$ group).

$R_3$ preferably represents an alkyl radical with 1 to 4 carbon atoms, such as methyl, ethyl, propyl, isopropyl, butyl, isobutyl, sec-butyl, tert-butyl.

The $R_3$ radical also preferably represents a phenyl radical that can possibly be substituted. It is necessary for this radical to be more deactivated than the aromatic compound, otherwise we would witness the acylation of the acylation agent itself.

As specific examples of substituents, we mention in particular:

a linear or branched alkyl radical with 1 to 6 carbon atoms, preferably 1 to 4 carbon atoms, such as methyl, ethyl, propyl, isopropyl, butyl, isobutyl, sec-butyl, tert-butyl, a linear or branched alkoxy radical with 1 to 6 carbon atoms, preferably 1 to 4 carbon atoms, such as the methoxy, ethoxy, propoxy, isopropoxy, butoxy, isobutoxy, sec-butoxy, and tert-butoxy radicals, a hydroxyl group, a halogen atom, preferably a fluorine, chlorine, or bromine atom.

The preferred acylation agents match formula (II) in which X' represents a chlorine atom and $R_3$ represents a methyl or ethyl radical.

When the acylation agent is an acid anhydride, the preferred compounds match formula (II) in which $R_3$ and $R_4$ are identical and represent an alkyl radical with 1 to 4 carbon atoms.

To give an idea of the acylation agents that match formula (II) we can the following in particular:

acetyl chloride, monochloroacetyl chloride, dichloroacetyl chloride, propanoyl chloride, isobutanoyl chloride, pivaloyl chloride, stearoyl chloride, crotonyl chloride, benzoyl chloride, chlorobenzoyl chloride, p-nitrobenzoyl chloride, methoxybenzoyl chloride, naphtoyl chloride, acetic anhydride, isobutyric anhydride, trifluoroacetic acid anhydride, benzoic anhydride, In accordance with the method described in the invention, the acylation reaction of an aromatic compound is performed in the presence of a catalyst, a bismuth salt of the trifluoromethanesulfonic acid.

The said acid can be used in its anhydrous or hydrated form.

The preferred catalyst in the invention's method matches the following formula:

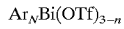 (IV)

In said formula (IV):

OTf represents $O_3SCF_3$,

Ar represents a monocyclic or polycyclic aromatic, carbocyclic radical, n is equal to 0, 1, or 2, Thus, in formula (IV), by "Ar" we mean, a monocyclic or polycyclic aromatic carbocyclic radical, possibly substituted, preferably with 6 to 18 carbon atoms.

We can mention in particular the phenyl or naphthyl radicals, possibly substituted, for example, by alkyl or alkoxy radicals with 1 to 4 carbon atoms, halogen atoms or trifluoromethyl groups. As Ar radicals, we preferably choose a phenyl or tolyl radical, or even more preferably a phenyl radical.

The catalysts susceptible of being used in the method described in the invention are either the tris-trifluoromethylsulfonate of bismuth with a formula of $Bi(OTf)_3$ or intermediate products of the bismuth triflate that match the following formulas: $Bi(OTf)Ar_2$ (IVa) and $Bi(OTf)_2Ar$ (IVb) and in particular $Bi(OTf)Ph_2$ and $Bi(OTf)_2Ph$.

It is also possible to use a mixture of said compounds.

As described above, the catalyst may be $Bi(OTf)_3$ where OTf represents $O_3SCF_3$. In more simple terms, we call it bismuth triflate. This product is a known product that is described in the literature. However, the formula (IV) compounds, in which n=1 and n=2, are new and are claimed as such.

In accordance with the acylation method of the invention, it is possible to use either the bismuth triflate or the new catalytic entities that match formulas (IVa) and (IVb). For language purposes, in the remainder of this document, "bismuth triflate" will designate both the tris-trifluoromethanesulfonate of bismuth and the intermediate products of formulas (IVa) and (IVb).

Remaining within the scope of the invention, we use a bismuth salt with a high degree of oxidation, for example 5, in which a triflate anion may be replaced by a metal atom, preferably monovalent and more particularly sodium and/or an oxygen atom. As examples of this type of catalyst, we cite, among others, $NaBi(SO_3CF_3)_4$ and $NaBiO(SO_3CF_3)_2$.

The invention includes any bismuth compound that contains a $R_F$—$SO_3$— radical in which $R_F$ represents a polyfluorinated alkyl radical with at least 1 carbon atom and up to a very high number of carbon atoms, as well as a polyfluorinated alkyl chain such as that found in a perfluorinated resin that bears sulfonic groups.

In accordance with the method of invention, the reaction between the aromatic compound and the acylation agent may be performed in the presence or in the absence of an organic solvent: where one of the reagents can be used as a reaction solvent.

A preferred variant of the method described in the invention consists of performing the reaction in an organic solvent.

It is preferable to select a solvent from the initial substrate and preferably an organic, polar, aprotic solvent.

As examples of polar, aprotic, organic solvents that may also be used in the invention's method, we can cite in particular linear or cyclic carboxamides such as N,N-dimethyl acetamide (DMAC), N,N-diethyl acetamide, dimethyl formamide (DMF), diethyl formamide, or 1-methyl-2-pyrrolidinone (NMP); nitrate compounds such as nitromethane, nitroethane, 1-nitropropane, 2-nitropropane or their mixes, nitrobenzene; aliphatic or aromatic nitriles such as acetonitrile, propionitrile, butanenitrile, isobutanenitrile, benzonitrile, benzyl cyanide; dimethylsulfoxyde (DMSO); tetramethylsulfone (sulfolane), dimethylsulfone, hexamethylphosphotriamide (HMPT); dimethylethylene urea , dimethylpropylene urea, tetramethylurea, propylene carbonate The preferred solvents are: nitromethane, nitroethane, 1-nitropropane, 2-nitropropane.

A mix of organic solvents can also be used.

The first stage of the invention's method consists of the acylation of the aromatic compound. In the next stage, a hydrolysis of the reaction mass obtained is performed.

The ratio between the aromatic compound's molar number and the acylation agent's molar number can vary because the substrate can be used as a reaction solvent. Thus, the ratio can range from 0.1 to 10, preferably from 1.0 to 4.0.

The quantity of catalyst used is determined in such a way that the ratio between the number of moles of catalyst and the number of moles of acylation agent is less than 1.0 and varies, preferably, between 0.001 and 0.8, and even more preferably between 0.02 and 0.2.

As far as the quantity of organic solvent used is concerned, it is usually chosen in such a way that the ratio between the number of moles of organic solvent and the number of moles of aromatic compound varies, preferably between 0 and 100 and even more preferably between 0 and 50.

The temperature at which the acylation reaction is performed depends on the reactivity of the starting substrate and of that of the acylation agent.

It is between 20° C. and 200° C., preferably between 40° C. and 150° C.

Usually, the reaction is conducted at atmospheric pressure, but higher or lower atmospheric pressures may also be used.

On a practical level, there are no constraints concerning the reagents. They can be introduced in any order.

After the reagents are placed in contact, the reaction mixture is brought to the desired temperature.

A variation to the invention consists in heating one of the reagents (acylation agent or aromatic compound) with the catalyst, and then introducing the other reagent.

The duration of the reaction depends on many parameters. In most cases it ranges from 30 minutes to 8 hours.

In the following step of the invention's method, a hydrolysis of the reaction mass obtained is performed.

The quantity of water used can vary greatly. The ratio between the number of moles of water and the number of moles of aromatic compound can range from 10 to 100, and preferably from 20 to 30.

With this end in view, a preferred implementation method consists in adding the reaction mass to a water bottom that has been brought to a temperature ranging between 0° and 100° C., preferably ranging between 150 and 30° C.

A variation of the invention consists in replacing the water with a basic solution, usually of soda, sodium carbonate or sodium hydrogen carbonate that has a weight concentration ranging from 5 to 20%.

The catalyst is separated, preferably by filtration. The catalyst can be recycled after drying.

At the end of the reaction, the desired product is retrieved, namely the aromatic ketone in organic phase.

The aqueous and organic phases are separated.

The organic phase is washed one or several times, preferably twice, with water.

The aqueous and organic phases are separated.

Then the aromatic ketone is retrieved from the organic phase according to known techniques, by elimination of the organic solvent, by distillation or by crystallization.

Another variant of the invention consists in retrieving the aromatic ketone directly, by distillation of the organic phase that contains the latter and the catalyst.

In accordance with the method described in the invention, the aromatic ketone retrieved is represented by the formula (III):

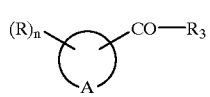

(III)

In said formula (III), A, R, $R_3$ and n have the same meaning as described previously.

Another element of this invention relates to the preparation of a catalyst that matches formula (IV).

It is advantageously prepared according to a new process that consists in performing a triarylbismuth and triflic acid reaction at low temperature.

Thus, in the formula (IV), by "Ar" we mean a monocyclic or polycyclic aromatic, carbocyclic radical, possibly substituted, having preferably from 6 to 18 carbon atoms.

More particularly phenyl or naphthyl radicals, that are possibly substituted, for example, by alkyl or alkoxy radicals with 1 to 4 carbon atoms, halogen atoms, of trifluoromethyl groups. As Ar radicals, we preferably choose a phenyl or tolyl radical, or even more preferably, a phenyl radical.

Triphenylbismuth is the preferred reagent.

The quantity of reagents used is usually such that the ratio between the number of moles of triflic acid and the number of moles of the triarybismuth is preferably selected between 0.9 and 3.1.

Depending on the quantity of triflic acid used, we then obtain a catalyst containing more or less triflate anions.

To obtain a catalyst of formula $Bi(OT)_3$, the quantity of triflic acid is between 2.9 and 3.1 moles by mole of triarylbismuth, and is preferably equal to 3.0.

According to a variation of the invention, as new products, we prepare intermediate products in the manufacturing of the triflate of bismuth that more specifically match the following formula:

(IV)

where n is equal to 1 or 2 and Ar and OTf have the same meaning as that given previously.

In particular, these compounds match the following formulas: $Bi(OTf)Ph_2$ and $Bi(OTf)_2Ph$, and are new products.

Their preparation depends on the quantity of triflic acid used. Therefore, for the formula (IV) catalysts where n is equal to 1 and which is illustrated by the formula (IVb), the quantity of triflic acid ranges from 1.9 to 2.1 moles, preferably with 2 moles for every mole of triarylbismuth. In the case of the formula (IV) catalysts where n is equal to 2 and which is illustrated by the formula (IVb), the quantity of triflic acid ranges from 0.9 to 1.1, with preferably 1 mole per mole of triarylbismuth.

The reaction to prepare the catalyst is usually performed in an organic solvent.

More specifically we use halogenated aliphatic hydrocarbons, preferably dichloromethane, chloroform, carbon tetrachloride, 1,2 dichloroethane.

The triarylbismuth is present in the organic solvent at a concentration level ranging preferably between 0.01 and 1 mole/liter.

According to a preferred implementation method, the triflic acid is progressively added to the solution that contains the triarylbismuth and the organic solvent.

As far as the temperature of the reaction is concerned, it is preferably chosen below 0° C. and even more preferably between −10° C. and −20° C.

At the end of the reaction, we let the reaction mixture return to room temperature (preferably between 15° C. and 25° C.) and obtain a bismuth triflate according to formula (IV) in a precipitated form.

Said precipitate is separated according to common liquid/solid separation techniques, preferably by filtration.

The catalyst prepared in this manner can be used in the acylation method of the invention.

The invention permits access to new catalysts, in particular, those of formulas (IVa) and (IVb). These catalysts present an interesting catalytic activity and have the advantage of not being as costly as the tris-trifluoromethanesulfonate of bismuth, because of the lesser quantity of trifluoromethanesolfonic acid required during preparation.

The following examples illustrate the invention without however setting any limits to it.

In these examples, the yields mentioned refer to this formula:

$$\text{Yield} = \frac{\text{Number of moles of aromatic ketones formed}}{\text{Number of moles of minority reactant}} \%$$

By "minority reactant", we mean either the aromatic substrate or the acylation agent, depending on the relative quantities of each that are added.

EXAMPLE 1
Synthesis of the Bismuth Triflate (III)

In a 250 ml balloon, purged with argon and equipped with an air entrance linked to a calcium chloride tube, we introduce, under magnetic agitation, 0.44 g of triphenylbismuth $Ph_3Bi$ (1 mmol) and 10 ml of anhydrous dichloromethane.

The solution is cooled to −78° C.

Using a syringe, we add 0.44 g of triflic acid (2.9 mmol).

A yellow coloring appears.

The reaction mixture is left to return to room temperature.

The solid obtained under argon is filtered and washed with dry dichloromethane in order to eliminate all traces of triflic acid.

The powder is put in a dual-neck balloon [bicol in French] and dried under reduced pressure (1 mm of mercury), under argon, for one hour.

The analysis of this powder by RMN $^{19}F(CD_3COCD_3)$ shows a high at 0.84 p.p.m., the RMN $^{13}F(CD_3COCD_3)$ shows a quartet at δ=120 p.p.m. ($^1J_{13C-19F}$=321 Hz).

Note the absence of protonic signal.

EXAMPLES 2 through 7
Acylation of the Anisole in the Presence of Bismuth Triflate.

Hereafter we describe the operating protocol that is used in the following examples.

In a 50 ml balloon purged with argon and equipped with a refrigeration system fitted with a calcium chloride exhaust tube, we insert the bismuth triflate (III), the substrate, and the acylation agent.

The proportions of the reagents are provided in the summary table that follows.

We use 10 mmol of substrate and 5 mmol of acylation agent for a molar ratio of 2.

The catalyst is introduced at the rate of 5% molar in relation to the substrate, or 0.16 g.

We possibly add 10 ml of solvent

The mixture is brought to the reaction temperature (generally the reflux) also mentioned in the summary table.

After cooling, we add 25 ml of water.

The organic products are removed with 2×15 ml of ethylic ether.

The organic phase, dried on sodium sulfate, is concentrated and analyzed by chromatography in gaseous phase.

The conditions and results are listed in table 1.

TABLE 1

| Ref Ex. | Acylation agent | Anisole/acylation agent molar ratio | Solvent | Temperature | Duration | Yield % |
|---|---|---|---|---|---|---|
| 2 | MeCOCl | 2 | $MeNO_2$ | 50° C. | 2 h | 80 |
| 3 | MeCOCl | 1 | No solvent | 50° C. | 3 h | 70 |
| 4 | $Me_2CHCOCl$ | 1 | No solvent | Reflux | 20 mn | 96 |
| 5 | PhCOCl | 1 | No solvent | Reflux | 2 h 30 mn | 81 |
| 6 | $(MeCO)_2O$ | 2 | $MeNO_2$ | Reflux | 4 h | 100 |
| 7 | $(MeCO)_2O$ | 1 | No solvent | Reflux | 1 h | 95 |

EXAMPLES 8 through 10

Acylation of Aromatic Hydrocarbons (halogenated or not) in the Presence of Bismuth Triflate.

In a 50 ml balloon purged with argon and equipped with a refrigeration system fitted with a calcium chloride exhaust tube, we insert 0.16 g (0.5 mmol) of bismuth triflate (III), 10 mmol of substrate (toluene, benzene, chlorobenzene) and 5 mmol of benzoyl chloride.

The mixture is heated under reflux for the duration indicated in the summary table that follows.

After a treatment performed according to examples 2 to 7, the reaction mixture is analyzed by RMN.

The conditions and results are listed in table II.

TABLE 2

| Ref Ex. | Substrate | Acylation agent | Substrate/acylation agent molar ratio | Solvent | Temperature | duration | Yield % |
|---|---|---|---|---|---|---|---|
| 8 | Toluene | PhCOCl | 2 | No Solvent | Reflux | 8 h | 70* |
| 9 | Benzene | PhCOCl | 2 | No Solvent | Reflux | 4 h | 95 |
| 10 | Chlorobenzene | PhCOCl | 2 | No Solvent | Reflux | 4 h | 60 |

*Proportion of ortho-para isomers = 25/75

Comparative test a

We operate as in sample 10 but using bismuth chloride $BiCl_3$ instead of bismuth triflate.

The conditions and the results are listed in table III.

TABLE III

| Ref Ex. | Substrate | Acylation agent | Substrate/ acylation agent molar ratio | Solvent | Temperature | duration | Yield % |
|---|---|---|---|---|---|---|---|
| a | Chlorobenzene | PhCOCl | 2 | No Solvent | Reflux | 4 h | 0 |

EXAMPLES 11 through 16

In the following examples, the benzoylation of various substrates is performed. These substrates are aromatic compounds that may or may not carry one or two substituents X and X' whose nature is detailed in table IV.

The reaction equation is as follows:

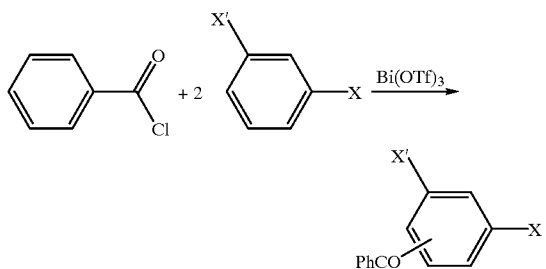

The required protocol used in these examples is described below:

In a 50 ml balloon that is mounted with a refrigerant and equipped with an exhaust tube filled with calcium chloride, we successively insert under argon, $Bi(OTf)_3$ (20 mmol), the substrate (200 mmol), and the benzoyl chloride (100 mmol).

The reaction mixture is placed in an oil bath at 140° C.: the temperature in the baloon ranges from 100 to 120° C.

The mixture is magnetically agitated for 4 hours.

The reaction's raw product is filtrated on silica gel (Silicagel Merck 60,230–400 mesh) with a pentane/ether mix (1/1) in order to eliminate the catalyst.

The solvents are evaporated under reduced pressure and the residue is analyzed in the gaseous phase by CPG chromatography performed on a Hewlett-Packard® GC 6890 chromatograph (capillary column HP5, 12 m×0.2 mm, film 5% phenylmethylsilicone) and by CPG-SM performed on a Hewlett-Packard® MS 5989 spectrometer coupled with a GC 5890 chromatograph (capillary column HP1, 12 m×0.2 mm, film 5% methylsilicone, electronic impact).

The results obtained are listed in table IV.

TABLE IV

| Ref Ex. | X | X' | Spreading rate | Selectivity o | m | p |
|---|---|---|---|---|---|---|
| 11 | OCH₃ | H | 74 | 8 | — | 92 |
| 12 | CH₃ | H | 95 | 19 | 2 | 79 |
| 13 | H | H | 78 | — | — | — |
| 14 | Cl | H | 89 | 13 | — | 87 |
| 15 | F | H | 86 | — | — | 100 |
| 16 | Cl | Cl | 37 | — | — | — |

EXAMPLES 17 and 18

In the following two examples, we prepare two catalysts, $Bi(OTf)Ph_2$ and $Bi(OTf)_2Ph$.

In order to do this, we repeat the process of example 1 with the exception that 1 mmol of triflic acid is introduced in example 17 and that 2 mmol of acid triflic is introduced in example 18.

The analysis by RMN [solvent $CD_3COCD_3$; δ in ppm, reference TMS ($^1H$, $^{13}C$), $CF_3COOH$ ($^{19}F$)] of the powder $Bi(OTf)Ph_2$ obtained according to example 17 is as follows:

RMN $^1H$: we distinguish 3 groups of signals for the aromatic protons: 7.45 ppn (multiplet, 1H, para), 8.28 (multiplet, 2H, meta), 9.28 (multiplet, 2H, ortho);

RMN $^{19}F$: a signal at 1.18 ppm (singlet)

RMN $^{13}C$: 120.9 ppm (quartet, J=321 Hz, $CF_3$)129.7, 133.1, 138.3 (3 aromatic CH carbons, the quaternary carbon does not appear).

The analysis by RMN of the $Bi(OTf)_2Ph$ powder obtained according to example 18 is as follows:

RMN $^1H$: we distinguish 3 groups of signals for the aromatic protons: 7.58 ppn (multiplet, 1H, para), 8.28 (multiplet, 2H, meta), 9.28 (multiplet, 2H, Ortho);

RMN $^{19}F$: a signal at 1.14 ppm (singlet, $CF_3$)

RMN $^{13}C$: 121.0 ppm (quartet, J=321 Hz, $CF_3$)130.4, 134.9, 139.1 (3 aromatic CH carbons, the quaternary carbon does not appear).

EXAMPLES 19, 20, and 21

We reproduce the operation protocol of examples 11 through 16 but we implement:
as a substrate: toluene
as an acylation agent: benzoyl chloride
as a catalyst:
in example 19: the catalyst from example 1,
in examples 20 and 21: the catalysts from examples 18 and 17.
reaction temperature is 120° C. and the duration is 4 hours.
following table shows the yields obtained:

TABLE V

| Ref. Ex. | Nature of the catalyst | Spreading Rate (%) |
|---|---|---|
| 19 | $Bi(OTf)_3$ | 95 |
| 20 | $Bi(OTf)_2Ph$ | 74 |
| 21 | $Bi(OTf)Ph_2$ | 73 |

Notice that the use of the intermediate products used in examples 20 and 21 show an interesting catalytic activity.

What is claimed is:

1. Aromatic compound acylation method comprising making an aromatic compound react with an acylation agent, in the presence of a catalyst wherein the acylation reaction is performed in the presence of an effective quantity of at least one bismuth salt of the triflic acid.

2. Method as set forth in claim 1, wherein the aromatic compound corresponds to the formula (I):

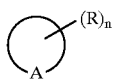 (I)

where:
A symbolizes the remainder of a cycle forming all or a part of a carbocyclic or heterocyclic, aromatic, monocyclic or polycyclic system: said cyclic remainder may carry a radical R representing a hydrogen atom or one or several identical or different substituents,
n represents the number of substituents on the cycle.

3. Method as set forth in claim 1, wherein the aromatic compound corresponds to the formula (I) in which the remainder A, optionally substituted, represents the remainder:
1) of a monocyclic or polycyclic aromatic carbocyclic compound,
2) of a monocyclic or polycyclic aromatic heterocyclic compound,
3) of a compound consisting of a chain of cycles, linked together:
by a covalent link
by an alkylene or alkylidene radical with 1 to 4 carbon atoms,
by one of the following groups

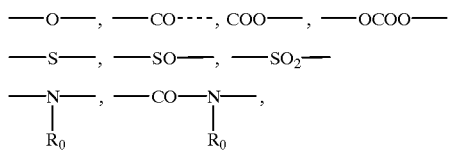

in these formulas, $R_0$ represents a hydrogen atom or an alkyl radical with 1 to 4 carbon atoms, a cyclohexyl or phenyl radical.

4. Method as set forth in claim 1, wherein the aromatic compound corresponds to the formula (I) in which the radical(s) R represent one of the following groups:
a hydrogen atom
a linear or branched alkyl radical, with 1 to 6 carbon atoms,
a linear or branched alkenyl radical with 2 to 6 carbon atoms,
a linear or branched alkoxy radical with 1 to 6 carbon atoms,
a cyclohexyl radical
an acyl group with 2 to 6 carbon atoms
a radical with a formula of:
$R_1$—OH
$R_1$—$COOR_2$
$R_1$—CHO
$R_1$—$NO_2$
$R_1$—CN
$R_1$—$(NR_2)_2$
$R_1$—CO—$(NR_2)_2$
$R_1$—X
R1—CF3
in these formulas, $R_1$ represents a covalent link or a divalent hydrocarbonic radical, linear or branched, saturated or unsaturated, with 1 to 6 carbon atoms; the identical or different $R_2$ radicals represent a hydrogen atom or a linear or branched alkyl radical with 1 to 6 carbon atoms; X symbolizes a halogen atom.

5. Method as set forth in claim 1, wherein the aromatic compound corresponds to the formula (I) in which, when n is greater than or equal to 2, two radicals R and the 2 successive atoms of the aromatic cycle can be linked to each other by an alkylene, alkenylene or alkenylidene radical that has 2 to 4 carbon atoms in order to form a saturated, unsaturated, or aromatic heterocycle that has 5 to 7 carbon atoms: one or several carbon atoms can be replaced by another heteroatom.

6. Method as set forth in claim 1, wherein the aromatic compound corresponds to the formula (I) in which:
the R radical(s) belong to one of the following groups:
a hydrogen atom,
an OH group,
a linear or branched alkyl radical that has 1 to 6 carbon atoms,
a linear or branched alkenyl radical that has 2 to 6 carbon atoms,
a linear or branched alkoxy radical that has 1 to 6 carbon atoms,
a —CHO group,
an acyl group that has 2 to 6 carbon atoms,
a —$COOR_2$ where $R_2$ has the same specifications as defined previously,
a —$NO_2$ group,
a —$NH_2$ group,
a halogen atom,
a —$CF_3$ group,
n is a number equal to either 0, 1, 2, or 3.

7. Method as set forth in claim 1, wherein the aromatic compound is a monocyclic or polycyclic aromatic carbocyclic compound with cycles that can form between themselves an orthocondensed system corresponding to formula (Ia):

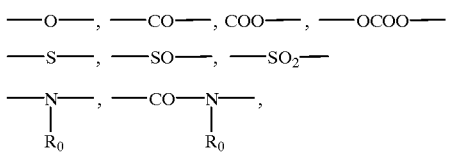

in this formula (Ia), m represents a number equal to 0, 1, or 2, R represents identical or different substituents, and n represents the number of said substituents.

8. Method as set forth in claim 7, wherein the aromatic compound corresponding to either formula (Ia) in which:
R represents a hydrogen atom, a hydroxyl group, a —CHO group, a —$NO_2$ group, a —$NH_2$ group, a linear or branched alkyl or alkoxy radical that has 1 to 6 carbon atoms,
m is equal to 0 or 1
n is equal to 0, 1 or 2,
p is equal to 0 or 1.

9. Method as set forth in claim 2, wherein the aromatic compound corresponding to formula (I) in which R represents a hydrogen atom, a hydroxyl group, a methyl radical, a methoxy radical, or a halogen atom.

10. Method as set forth in claim 1, wherein the aromatic compound is either benzene, toluene, phenol, anisole, or veratrole.

11. Method as set forth in claim 1, wherein the acylation agent corresponds to formula (II):

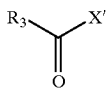

(II)

where:
R₃ represents:
a saturated or unsaturated, linear or branched aliphatic radical, that has 1 to 24 carbon atoms; a saturated, unsaturated, or aromatic, monocyclic or polycyclic cycloaliphatic radical that has 4 to 12 carbon atoms; a saturated or unsaturated, linear or branched aliphatic radical bearing a cyclic substitutent,
X' represents:
a halogen atom,
a —O—CO—R₄ radical with R₄ being identical to or different from R₃, with the same specification as R₃.

12. Method as set forth in claim 11 wherein the acylation agent matches formula (II) wherein X' represents a chlorine atom and R₃ represents a linear or branched alkyl radical that has 1 to 12 carbon atoms: the hydrocarbonic chain being optionally interrupted by a heteroatom or by a functional group or a group bearing a substitutent; R₃ represents a phenyl radical that is optionally substituted; where X' represents a radical —O—CO—R₄ in which R₃ and R₄ are identical and represent an alkyl radical that has 1 to 4 carbon atoms.

13. Method as set forth in claim 11, wherein the acylation agent comprises:
acetyl chloride,
monochloroacetyl chloride,
dichloroacetyl chloride,
propanoyl chloride,
isobutanoyl chloride,
pivaloyl chloride,
stearoyl chloride,
crotonyl chloride,
benzoyl chloride,
chlorobenzoyl chloride,
p-nitrobenzoyl chloride,
methylbenzoyl chloride,
naphthoyl chloride,
acetic anhydride,
isobutyric anhydride,
trifluoroacetic anhydride, or
benzoic anhydride.

14. Method as set forth in claim 1, wherein the reaction solvent is one of the reagents or an organic, aprotic polar solvent.

15. Method as set forth in claim 14 wherein organic solvent comprises linear or cyclic carboxamides; nitrate compounds, aliphatic or aromatic nitriles, dimethylsulfoxide (DMSO); tetramethylsulfone (sulfolane), dimethylsulfone, hexamethylphosphotriamide (HMPT); dimethylethylene urea, dimethylpropylene urea, tetramethyl urea, propylene carbonate or their mixtures.

16. Method as set forth of claim 1, wherein the ratio between the aromatic compound's molar number and the acylation agent's molar number falls between 0.1 and 10.

17. Method as set forth of claim 1, wherein the ratio between the number of moles of catalyst and the number of moles of acylation agent is less than 1.0.

18. Method as set forth of claim 1, wherein the temperature during the acylation reaction is set between 20° C. and 200° C.

19. Method as set forth of claim 1, wherein the catalyst contains at least one bismuth salt of the triflic acid that corresponds formula (IV):

$$Ar_nBi(OTf)_{3-n} \quad (IV)$$

in said formula (IV):
OTf represents $O_3SCF_3$,
Ar represents a monocyclic or polycyclic aromatic carbocyclic radical,
n is equal to 0, 1, or 2.

20. Method as set forth in claim 19 wherein the bismuth salt of the triflic acid corresponds formula (IV) in which Ar represents a phenyl or naphthyl radical that is optionally substituted by alkyl or alkoxy radicals that have 1 to 4 carbon atoms, halogen atoms, or trifluoromethyl groups.

21. Method as set forth in claim 1, wherein the catalyst comprises $Bi(OTf)_3$, $Bi(OTf)_2Ph$, $Bi(OTf)Ph_2$ or their mixtures.

22. Bismuth salt of the triflic acid that corresponds to formula (IV):

$$A_nBi(OTf)_{3-n} \quad (IV)$$

in said formula (IV):
OTf represents $O_3SCF_3$,
Ar represents a monocyclic or polycyclic aromatic carbocyclic radical,
n is equal to 1, or 2.

23. Bismuth salt of the triflic acid as set forth in claim 22, wherein it corresponds to formula (IV) wherein Ar represents a phenyl or naphthyl radical that is optionally substituted by alkyl or alkoxy radicals that have 1 to 4 carbon atoms, halogen atoms, or trifluoromethyl groups.

24. Bismuth salt of the triflic acid of formula $Bi(OTf)_2Ph$ or $Bi(OTf)Ph_2$.

25. Method of preparation of the tris-trifluoromethanesulfonate of bismuth comprising making a triarylbismuth and the triflic acid react at a temperature lower than 0° C.

26. Method as set forth in claim 25 wherein the ratio between the number of moles of triflic acid and the number of moles of triarylbismuth is chosen between 2.9 and 3.1.

27. Method of preparation of the bismuth salt of the triflic acid matching formula $Ar_n(OTf)_{3-n}$ (IV) comprising making a triarybismuth and the triflic acid react at a temperature lower than 0° C.

28. Method as set forth in claim 27 wherein the ratio between the number of moles of triflic acid and the number of moles of triarylbismuth is between 1.9 and 2.1, for the bismuth salt of formula (IV) in which n is equal to 1, and between 0.9 and 1.1, for the bismuth salt of formula (IV) in which n is equal to 2.

29. Method as set forth in claim 25, wherein the triarylbismuth is a triphenylbismuth.

30. Method as set forth in claim 25, wherein the triflic acid is progressively added to the triarylbismuth.

31. Method as set forth in claim 25, wherein the reaction is performed in an organic solvent.

32. Method as set forth in claim 25, wherein the triarylbismuth is present in the organic solvent at a concentration rate between 0.01 and 1 mole/liter.

33. Method as set forth in claim 25, wherein the temperature of the reaction is between −100° C. and −20° C.

34. Method as set forth in claim 1, wherein the aromatic compound is a compound made by linking two or several monocyclic aromatic carbocycles corresponding to formula (Ib):

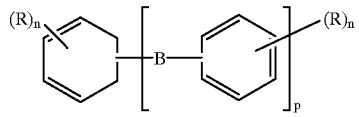

in this formula (Ib), represents identical or different substituents and n represents the number of said substituents, p is a number equal to 0, 1, 2, or 3 and B represents:

a covalent link an alkylene or alkylidene radical that has 1 to 4 carbon atoms, one of the following groups

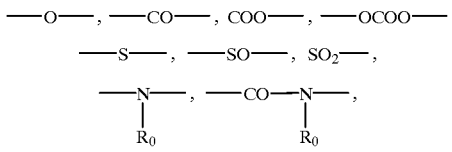

in these formulas, $R_0$ represents a hydrogen atom or an alkyl radical that has 1 to 4 carbon atoms, a cyclohexyl or phenyl radical.

* * * * *